United States Patent [19]

Kummer et al.

[11] Patent Number: 4,505,912
[45] Date of Patent: Mar. 19, 1985

[54] 5-ANILINO-1,2,3-TRIAZOLE-4-CARBOXYLIC ACID COMPOUNDS

[75] Inventors: Werner Kummer; Herbert Köppe; Helmut Stähle, all of Ingelheim am Rhein; Richard Reichl; Franz J. Kuhn, both of Gau-Algesheim, all of Fed. Rep. of Germany

[73] Assignee: Boehringer Ingelheim KG, Ingelheim am Rhein, Fed. Rep. of Germany

[21] Appl. No.: 410,008

[22] Filed: Aug. 20, 1982

[30] Foreign Application Priority Data

Sep. 3, 1981 [DE] Fed. Rep. of Germany ....... 3134842

[51] Int. Cl.³ .................. A61K 31/41; C07D 249/04; C07D 401/06; C07D 413/06
[52] U.S. Cl. ..................... 514/236; 548/255; 544/132; 546/208; 514/326; 514/359
[58] Field of Search ............ 548/255; 544/132; 546/208; 424/232, 253, 267, 248.55, 269

[56] References Cited

U.S. PATENT DOCUMENTS 2,714,110  7/1955  Webb et al. ............ 548/255

FOREIGN PATENT DOCUMENTS 7002572  8/1970  Netherlands ............ 548/255

Primary Examiner—Alton D. Rollins

Attorney, Agent, or Firm—Hammond & Littell, Weissenberger & Dippert

[57] ABSTRACT

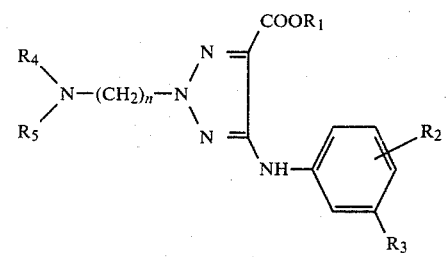

wherein
$R_1$ is straight or branched alkyl of 1 to 4 carbon atoms;
$R_2$ is hydrogen, halogen, amino, nitro, alkoxy of 1 to 3 carbon atoms, —$COOR_6$, 3-methyl or 4-methyl;
$R_4$ and $R_5$ are each alkyl of 1 to 4 carbon atoms or, together with each other and the nitrogen atom to which they are attached, piperidino, pyrrolidino or morpholino;
$R_6$ is alkyl of 1 to 3 carbon atoms; and
n is 2 or 3;

and non-toxic, pharmacologically acceptable acid addition salts thereof. The compounds as well as their salts are useful as sleep potentiators and blood circulation enhancers.

6 Claims, No Drawings

5-ANILINO-1,2,3-TRIAZOLE-4-CARBOXYLIC ACID COMPOUNDS

This invention relates to novel derivatives of anilino-1,2,3-triazole and acid addition salts thereof, to a method of preparing these compounds, to pharmaceutical compositions containing them as active ingredients, and to methods of using them as sleep-potentiators and circulation enhancers.

More particularly, the present invention relates to a novel class of compounds represented by the generic formula

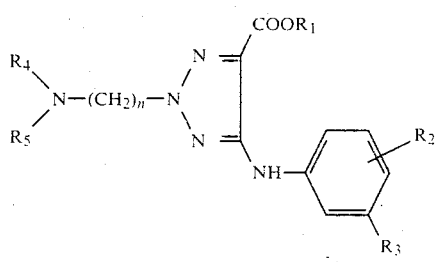

wherein $R_1$ is straight or branched alkyl of 1 to 4 carbon atoms;

$R_2$ is hydrogen, halogen, amino, nitro, alkoxy of 1 to 3 carbon atoms, —$COOR_6$, 3-methyl or 4-methyl;

$R_3$ is hydrogen or halogen;

$R_4$ and $R_5$ are each alkyl of 1 to 4 carbon atoms or, together with each other and the nitrogen atom to which they are attached, piperidino, pyrrolidino or morpholino;

$R_6$ is alkyl of 1 to 3 carbon atoms; and n is 2 or 3;

and non-toxic, pharmacologically acceptable acid addition salts thereof.

A preferred subgenus thereunder is constituted by compounds of the formula

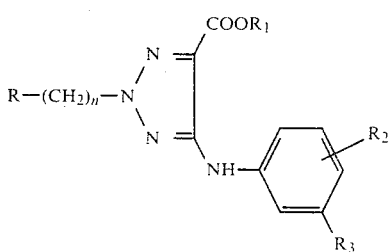

wherein

R is dimethylamino, diethylamino, piperidino or morpholino;

$R_1$ is straight or branched alkyl of 1 to 4 carbon atoms;

$R_2$ is hydrogen, chlorine, 3-methyl, 4-methyl, methoxy, nitro, amino, methoxycarbonyl, 4-fluoro or 4-bromo;

$R_3$ is hydrogen or chlorine; and n is 2 or 3;

and non-toxic, pharmacologically acceptable acid addition salts thereof.

A particularly preferred subgenus is constituted by those compounds of the formula Ia wherein R, $R_2$, $R_3$ and n have the same meanings as in formula Ia, and $R_1$ is methyl, ethyl or n-butyl, and non-toxic, pharmacologically acceptable acid addition salts thereof.

An especially preferred subgenus is constituted by those compounds of the formula Ia wherein R is dimethylamino or diethylamino;

$R_1$ is methyl or n-butyl;

$R_2$ is methyl, 4-chloro or 4-bromo;

$R_3$ is hydrogen; and n is 2 or 3;

and non-toxic, pharmacologically acceptable acid addition salts thereof.

The compounds embraced by formula I above may be prepared by the method represented by the following schematic reaction sequence:

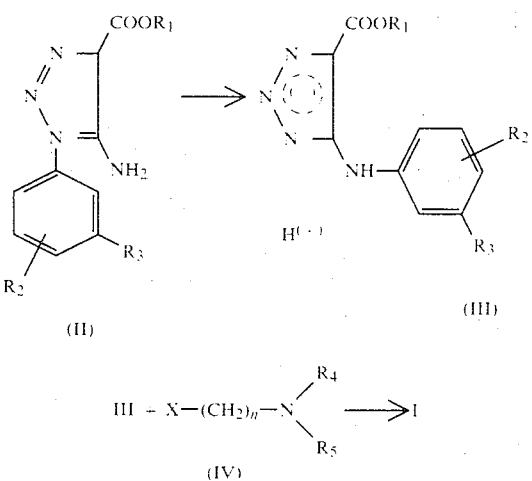

Thus, a triazole derivative of the formula III, wherein $R_1$, $R_2$ and $R_3$ have the meanings previously defined, is reacted with a compound of the formula IV wherein $R_4$ and $R_5$ have the meanings previously defined and X is halogen. The reaction is preferably performed in an aprotic polar solvent in the presence of a base such as sodium carbonate. The optimum reaction period and reaction temperature depend upon the nature of substituents $R_1$ to $R_5$ and X, and may vary over a wide range.

The starting compounds of the formula III, some of which are known, are obtained by subjecting a corresponding 1-phenyl-5-amino-1H-1,2,3-triazol-4-carboxylic acid ester of the formula II to a Dimroth rearrangement [Annalen 364, 183 (1909); and 459, 39 (1927)].

This rearrangement is brought about by simply heating compound II with a polar solvent, particularly when a base is added, which means that the reaction of the compound of the formulas III and IV may most advantageously be effected by using the 1-phenyl-5-amino-1H-1,2,3-triazol-4-carboxylic acid ester of the formula II without isolation of the compound of the general formula III formed by the rearrangement.

The compounds embraced by formula I are basic and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxy-benzoic acid, p-aminobenzoic acid, phthalic acid, cinnamic acid, salicylic acid, ascorbic acid, methanesulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1 n-Butyl 2-(3-piperidino-propyl)-5-(4-tolylamino)-2H-1,2,3-triazole-4 carboxylate hydrochloride

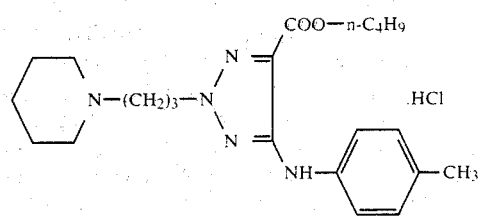

A mixture consisting of 8.2 gm (0.03 mol) of n-butyl 1-(4-tolyl)-5-amino-1H-1,2,3-triazole-4-carboxylate, 100 ml of absolute dimethyl formamide and 14.6 gm (0.09 mol) of 3-chloropiperidino-propane was stirred at 100° C. for 4 hours. The resulting solution was then evaporated in vacuo, the residue was dissolved in 2N-hydrochloric acid, and the acid solution was fractionally extracted with ether at stepwisely increasing pH values. The ether extracts with a pH of 5 were isolated and evaporated, the residue was dissolved in ethanol, and the hydrochloride was precipitated with ethereal hydrochloric acid. The hydrochloride was then fractionally re-precipitated from alcohol/ether.

1.9 gm of the desired compound was obtained, corresponding to 14.6% of theory, with a melting point of 148° C.

EXAMPLE 2 n-Butyl 2-(3-dimethylamino-propyl)-5-(4-bromophenylamino)-2H-1,2,3-triazole-4-carboxylate hydrochloride A mixture consisting of 8.5 gm (0.025 mol) of n-butyl 1-(4-bromophenyl)-5-amino-1H-1,2,3-triazole-4-carboxylate, 100 ml of absolute dimethylformamide and 9.1 gm (0.075 mol) of 1-chloro-3-(N,N-dimethylamino)-propane was reacted and worked up as in Example 1.

1.5. gm of the desired compound were obtained, corresponding to 13% of theory, with a melting point of 158° C.

EXAMPLE 3 n-Butyl 2-(2-dimethylamino-ethyl)-5-(4-chlorophenylamino)-2H-1,2,3-triazole-4-carboxylate hydrochloride A mixture consisting of 6.0 gm (0.02 mol) of n-butyl 1-(4-chlorophenyl)-5-amino-1H-1,2,3-triazole-4-carboxylate, 100 ml of absolute dimethylformamide and 4.3 gm (0.04 mol) of 1-chloro-2-dimethylamino-ethane was reacted as in Example 1, the reaction mixture was evaporated, the residue was dissolved in 2N hydrochloric acid and water, and the solution was extracted with ether at stepwisely increasing pH values. After evaporation of those ether phases shown to be pure by thin-layer chromatography, the residue was dissolved in a little isopropanol, the solution was acidified with ethereal hydrochloric acid, and the hydrochloride was precipitated with ethyl acetate. After recrystallization from ethanol, 0.8 gm of the desired compound, corresponding to 9.9% of theory, was obtained with a melting point of 171° C.

EXAMPLE 4 n-Butyl 21-(2-dimethylamino-ethyl)-5-(4-chlorophenylamino)-2H-1,2,3-triazole-4-carboxylate hydrochloride 8.4 gm (0.025 mol) of n-butyl 1-acetyl-5-(4-chlorophenylamino)-1H-1,2,3-triazole-4-carboxylate were added to a solution of 2 gm (0.05 mol) of sodium hydroxide in 40 ml of distilled water, and the mixture was stirred at room temperature for 30 minutes. 60 ml of toluene and 10 mg of 18-crown-6-ether were added to the resulting deacetylated compound, and then 3.3 gm (0.024 mol) of diethylaminoethyl chloride were added dropwise thereto over a period of 2 minutes. The mixture was then stirred at room temperature for one hour, another 3.3 gm (0.024 mol) of diethylaminoethyl chloride were added dropwise thereto, and the resulting mixture was stirred for one hour at 35° to 40° C. and then for one hour at 60° C.

The toluene and water phases were separated and the toluene phase was extracted first with water and then with water/2N hydrochloric acid. Three phases were thus formed, namely toluene, water and oil. The oil was separated, dissolved in 2N hydrochloric acid, and the solution was extracted several times with ether. The toluene and ether phases were discarded. The water phases were combined and extracted with ether at stepwisely increasing pH values. The ether with a pH of 5 was dried over sodium sulfate, evaporated in vacuo and the residue was dissolved in a little ethyl acetate.

The hydrochloride was precipitated with ethereal hydrochloric acid and recrystallized from isopropanol.

1.6. gm of the desired compound were obtained, corresponding to 14.5% of theory, with a melting point of 170° C.

EXAMPLE 5

Ethyl 2-(2-diethylamino-ethyl-5-(4-chlorophenylamino)-2H-1,2,3-triazole-4-carboxylate hydrochloride A mixture consisting of 5.4 gm (0.02 mol) of ethyl 1-(4-chlorophenyl-5-amino-1H-1,2,3-triazole-4-carboxylate, 100 ml of absolute dimethyl formamide and 5.4 gm (0.04 mol) of diethylaminoethyl chloride was reacted and worked up as in Example 3.

1.4 gm of the desired compound were obtained, corresponding to 17.4% of theory, with a melting point of 178° C.

EXAMPLE 6

Ethyl 2-(3-morpholino-propyl)-5-(4-chlorophenylamino-2H-1,2,3-triazole-4-carboxylate hydrochloride A mixture consisting of 5.4 gm (0.02 mol) of ethyl 1-(4-chlorophenyl)-5-amino-1H-1,2,3-triazole-4-carboxylate, 100 ml of absolute dimethyl formamide and 8.9 gm (0.05 mol) of 1-chloro-3-morpholino-propane was reacted as in Example 1, the resulting solution was evaporated, and the residue was dissolved in 2N hydrochloric acid and water. The solution was extracted with ether at stepwisely increasing pH values up to pH 9, and the ether phases shown to the pure by thin-layer chromatography were combined, dried over sodium sulfate and evaporated in vacuo. The residue was dissolved in chloroform, the solution was acidified with ethereal hydrochloric acid, and the hydrochloride was precipitated with ether and re-crystallized twice from ethanol. 0.8 gm, corresponding to 9.3% of theory, of the desired compound was obtained; melting point 223° C.

EXAMPLE 7

Methyl 2-(2-diethylamino-ethyl)-5-(4-chlorophenylamino)-2H-1,2,3-triazole-4-carboxylate hydrochloride A mixture of consisting of 5.1 gm (0.02 mol) of methyl 1-(4-chlorophenyl)-5-amino-1H-1,2,3-triazole-4-carboxylate, 50 ml of absolute dimethyl formamide and 2.1 gm (0.02 mol) of anhydrous sodium carbonate was stirred at room temperature for 5 minutes. 2.7 gm (0.02 mol) of 1-diethyl-amino-3-chloro-ethane were added, the mixture was stirred at 100° C. for 3 hours, and then the solvent was evaporated in vauco. The residue was dissolved in 2N hydrochloric acid, the solution was fractionally extracted with ether at pH 2 to pH 6, and the ether phases shown to be pure by thin-layer chromotography were combined, dried over sodium sulfate and evaporated in vacuo. The residue was dissolved in a little methanol, the solution was acidified with ethereal hydrochloric acid, and the hydrochloride was precipitated with ether.

2.4 gm of the desired compound were obtained, corresponding to 30.9% of theory, with a melting point of 180° C.

EXAMPLE 8

Methyl 2-(3-diethylamino-propyl)-5-(4-chlorophenylamino)-2H-1,2,3-triazole-4-carboxylate hydrochloride A mixture consisting of 5.1 gm (0.02 mol) of methyl 1-(4-chlorophenyl)-5-amino-1H-1,2,3-triazole-4-carboxylate, 100 ml of absolute dimethyl formamide and 7.5 gm (0.05 mol) of 1-chloro-3-diethylamino-propane was reacted analogous to Example 1, the reaction mixture was evaporated in vacuo, the residue was dissolved in 2N hydrochloric acid, and the solution was fractionally extracted with ether at stepwisely increasing pH values. After evaporation of the ether phases which were shown to be identical and pure by thin-layer chromatography, the residue was dissolved in ethyl acetate, and the hydrochloride was precipitated with ethereal hydrochloric acid and recrystallized twice, yielding 1.1 gm of the desired compound, corresponding to 13.7% of theory; melting point 181° C.

EXAMPLE 9

Methyl 2-(3-dimethylamino-propyl)-5-(4-chlorophenylamino)-2H-1,2,3-triazole-4-carboxylate hydrochloride A mixture consisting of 5.1 gm (0.02 mol) of methyl 1-(4-chlorophenyl)-5-amino-1H-1,2,3-triazole-4-carboxylate, 100 ml of absolute dimethyl formamide and 6.1 gm (0.05 mol) of 1-chloro-3-dimethylamino-propane was reacted and worked up as in Example 8.

1.4 gm (18.7% of theory) of the desired compound were obtained; melting point 197° C.

EXAMPLE 10

Methyl 2-(3-morpholino-propyl)-5-(4-chlorophenylamino)-2H-1,2,3-triazole-4-carboxylate hydrochloride A mixture consisting 7.6 gm (0.03 mol) of methyl 1-(4-chlorophenyl)-5-amino-1H-1,2,3-triazole-4-carboxylate, 100 ml of absolute dimethylformamide and 16.2 gm (0.09 mol) of 1-chloro-3-morpholino-propane was reacted and worked up as in Example 1.

1.0 gm (8% of theory) of the desired compound was obtained; melting point 217° C.

EXAMPLE 11

Methyl 2-(2-diethylamino-ethyl)-5-(4-fluorophenylamino)-2H-1,2,3-triazole-4-carboxylate hydrochloride A mixture consisting of 4.7 gm (0.02 mol) of methyl 1-(4-fluorophenyl)-5-amino-1H-1,2,3-triazole-4-carboxylate, 70 ml of absolute dimethyl formamide and 8.1 gm (0.06 mol) of 1-chloro-2-diethylamino-ethane was reacted as in Example 1. The reaction mixture was then evaporated in vacuo and the residue was dissolved in 2N hydrochloric acid. The solution was extracted with chloroform, filtered through activated charcoal, dried over sodium sulfate, and the chloroform was distilled off in vacuo. After recrystallization from isopropanol, 1.5 gm (20.2% of theory) of the desired compound were obtained; melting point 179° C.

EXAMPLE 12

Methyl 2-(2-diethylamino-ethyl)-5-(4-bromophenylamino)-2H-1,2,3-triazole-4-carboxylate hydrochloride A mixture consisting of 6.5 gm (0.022 mol) of methyl 1-(4-bromophenyl)-5-amino-1H-1,2,3-triazole-4-carboxylate, 100 ml of dimethylformamide and 8.9 gm (0.066 mol) of 1-chloro-2-diethylamino-ethane was reacted and worked up as in Example 11.

2.3 gm of the desired compound were obtained (24.2% of theory); melting point 199° C.

EXAMPLE 13

Methyl 2-(2-diethylamino-ethyl)-5-(3-chloro-4-methyl-phenylamino)-2H-1,2,3-triazole-3-carboxylate hydrochloride A mixture consisting of 5 gm (0.019 mol) of methyl 1-(3-chloro-4-methylphenyl)-5-amino-1H-1,2,3-triazole-4-carboxylate, 100 ml of absolute dimethylformamide and 7.7 gm (0.057 mol) of 1-chloro-2-diethylamino-ethane was reacted and worked up as in Example 9.

1.0 gm (corresponding to 13.1% fo theory) of the desired compound eas obtained; melting point 182° C.

EXAMPLE 14

Methyl 2-(2-diethylamino-ethyl)-5-(3,4-dichlorophenylamino)-2H-1,2,3-triazole-4-carboxylate maleate A mixture consisting of 8.6 gm (0.03 mol) of methyl 1-(3,4-dichloropheynyl)-5-amino-1H-1,2,3-triazole-4-carboxylate, 100 ml of absolute dimethylformamide, 8.1 gm (0.06 mol) of 1-chloro-2-diethylamino-ethane and 10 mg of 18-crown-6-ether was reacted as in Example 1.

The reaction mixture was evaporated in vacuo and the residue was stirred with 2N sodium hydroxide. The mixture was then extracted with chloroform, slowly suction-filtered through aluminum oxide and charcoal, and evaporated in vacuo. The residue was dissolved in ethanol, the solution was acidified with ethanolic maleic acid, and the maleate was precipitated with ether.

1.0 gm of the desired compound (corresponding to 6.6% of theory) was obtained; melting point 135° C.

EXAMPLE 15

Methyl 2-(3-diethylamino-propyl)-5-(3,4-dichlrophenylamino)-2H-1,2,3-triazole-4-carboxylate oxalate 5.8 gm (0.02 mol) of methyl 1-(3,4-dichlorophenyl)-5-amino-1H-1,2,3-triazole-4-carboxylate were introduced into 80 ml of absolute dimethyl formamide, and 0.8 gm of a 55% sodium hydride dispersion was added in batches. A clear solution was thus formed, and the temperature rose from 20° C. to 25° C. Then, 3 gm (0.02 mol) of 1-chloro-3-diethylaminopropane were added, and the resulting mixture was stirred at room temperature for 16 hours. The solvent was then distilled off in vacuo, the residue was stirred with 2N hydrochloric acid, and the undissolved matter was suction-filtered off. The filtrate was fractionally extracted with ether at stepwise increasing pH values, and the ether phases found to be pure by thin-layer chromatography were combined, dried over sodium sulfate and evaporated in vacuo. The residue was dissolved in ethanol, the solution was acidified with ethanolic oxalic acid, and the precipitated oxalate was recrystallized from ethanol.

1.2 gm (12.3% of theory) of the desired compound were obtained; melting point 148° C.

EXAMPLE 16

Methyl 2-(2-diethylamino-ethyl)-5-(3,5-dichlorophenylamino)-2H-1,2,3-triazole-4-carboxylate hydrochloride A mixture consisting of 5.8 gm (0.02 mol) methyl 1-(3,5-dichlorophenyl)-5-amino-1H-1,2,3-triazole-4-carboxylate, 80 ml of absolute dimethylformamide, 0.8 gm of 55% sodium hydride dispersion, 2.7 gm (0.02 mol) of 1-chloro-2-diethylaminoethane and 10 mg of 18-crown-6-ether was reacted and worked up as in Example 15.

1.5 gm (15.8% of theory) of the desired compound were obtained; melting point 188° C.

EXAMPLE 17

Methyl 2-(3-diethylamino-propyl)-5-(3,5-dichloro-phenylamino)-2H-1,2,3-triazole-4-carboxylate hydrochloride A mixture consisting of 5.8 gm (0.02 mol) of methyl 1-(3,5-dichlorophenyl)-5-amino-1H-1,2,3-triazole-4-carboxylate, 80 ml of absolute dimethylformamide, 0.8 gm of sodium hydride dispersion and 3.0 gm (0.02 mol) of 1-chloro-3-diethylamino-propane was reacted and worked up as in Example 15.

0.9 gm (9.2% of theory) of the desired compound was obtained; melting point 158° C.

EXAMPLE 18

Methyl 2-(2-diethylamino-ethyl)-5-(3,4-dichlorophenylamino)-2H-1,2,3-triazole-4-carboxylate hydrochloride 5.8 gm (0.02 mol) of methyl 1-(3,4-dichlorophenyl)-5-amino-1H-1,2,3-triazole-4-carboxylate were stirred with 2.3 gm (0.02 mol) of potassium tert. butoxide in 100 ml of absolute dimethyl formamide for 1 hour at 100° C. The mixture was then cooled to 20° C., and 2.2 gm (0.02 mol) of 1-chloro-2-dimethylamino-ethane were added thereto. The resulting mixture was stirred at 100° to 120° C. for 3 hours, the solvent was then distilled off in vacuo, and the residue was dissolved in 2N hydrochloric acid. The solution was fractionally extracted with ether, the desired ether phases were dried and evaporated in vacuo, and the residue was dissolved in ethanol. The solution was acidified with ethereal HCl, the hydrochloride was precipitated with ether, and the crystals were recrystallized twice from alcohol.

0.3 gm (4% of theory) of the desired compound was obtained; melting point 200° C.

EXAMPLE 19

Methyl 2-(2-dimethylamino-ethyl)5-(3,5-dichloro-phenylamino)-2H-1H-1,2,3-triazole-4-carboxylate hydrochloride 5.8 gm (0.02 mol) of methyl 1-(3,5-dichlorophenyl)-5-amino-1H-1,2,3-triazole-4-carboxylate were added to 100 ml of absolute dimethyl formamide and reacted with 2.3 gm (0.02 mol) of potassium tert. butoxide and 2.2 gm (0.02 mol) of 1-chloro-2-dimethylamino-ethane, and the reaction mixture was worked up, as described in Example 18.

0.3 gm (4% of theory) of the desired compound was obtained; melting point 212° C.

EXAMPLE 20

Methyl 2-(2-dimethylamino-ethyl)-5-(4-chlorophenylamino)-2H-1,2,3-triazole-4-carboxylate hydrochloride 5.1 gm (0.02 mol) of methyl 1-(4-chlorophenyl)-5-amino-1H-1,2,3-triazole-4-carboxylate were added to 100 ml of absolute dimethylformamide and reacted with 2.3 gm (0.02 mol) of potassium tert. butoxide and 2.2 gm (0.02 mol) of 1-chloro-2-dimethylamino-ethane, and worked up as in Example 18.

0.8 gm (11% of theory) of the desired compound was obtained; melting point 205° C.

EXAMPLE 21

Methyl 2-(2-diethylamino-ethyl)-5-(4-methoxyphenylamino)-2H-1,2,3-triazole-4-carboxylate hydrochloride 10.0 gm (0.04 mol) of methyl 1-(4-methoxyphenyl)-5-amino-1H-1,2,3-triazole-4-carboxylate were added to 200 ml of absolute dimethylformamide and reacted with 4.5 gm (0.04 mol) of potassium tert. butoxide and 5.4 gm (0.04 mol) of 1-chloro-2-diethylamino-ethane, and worked up as in Example 18.

1.2 gm (7.8% of theory) of the desired compound were obtained; melting point 145° C.

EXAMPLE 22

8.7 gm (0.04 mol) of methyl 1-phenyl-5-amino-1H-1,2,3-triazole-4-carboxylate were added to 150 ml of absolute dimethylformamide and reacted with 4.5 gm (0.04 mol) of potassium tert. butoxide and 5.5 gm (0.04 mol) of 1-chloro-2-diethylamino-ethane, and worked up as in Example 18, except that the base was dissolved in isopropanol, and the salt was formed with ethereal HCl and precipitated with ethyl acetate. The crystals were re-precipitated from ethanol/ether.

2.3 gm (16% of theory) of the desired compound were obtained; melting point 150° C.

EXAMPLE 23

Methyl 2-(2-dimethylamino-ethyl)-5l-(3-chloro-4-methyl-phenylamino)-2H-1,2,3-triazole-4-carboxylate hydrochloride 5.4 gm (0.02 mol) of methyl 1-(3-chloro-4-methyl-phenyl)-5-amino-1H-1,2,3-triazole-4-carboxylate were introduced into 100 ml of absolute dimethylformamide and reacted with 2.3 gm (0.02 mol) of potassium tert. butoxide and 2.2 gm (0.02 mol) of 1-chloro-2-dimethylamino-ethane, and worked up as described in Example 22 or 18.

0.7 gm (9.35% of theory) of the desired compound was obtained; melting point 191° C.

EXAMPLE 24

Methyl 2-(2-diethylamino-ethyl)-5-(4-nitrophenylamino)-2H-1,2,3-triazole-4-carboxylate hydrochloride 43.4 gm (0.165 mol) of methyl 1-(4-nitrophenyl)-5-amino-1H-1,2,3-triazole-4-carboxylate were introduced into 300 ml of absolute dimethylformamide and reacted with 18.5 gm (0.165 mol) of potassium tert. butoxide and 22.35 gm (0.165 mol) of 1-chloro-2-diethylamino-ethane as in Example 18. Then, the solvent was distilled off, and the residue was dissolved in 2N hydrochloric acid. Fractional precipitation was effected with 2N sodium hydroxide. The base was suction-filtered off and dissolved in ethanol, and the salt was precipitated with ethereal HCl.

4.6 gm (7% of theory) of the desired compound were obtained; melting point 195° C.

EXAMPLE 25

Methyl 2-(2-diethylamino-ethyl)-5-(4-aminophenylamino)-2H-1,2,3-triazole-4-carboxylate dihydrochloride 4.2 gm (0.01 mol) of methyl 2-(2-diethylaminoethyl)-5-(4-nitrophenylamino)-2H-1,2,3-triazole-4-carboxylate were hydrogenated in 80 ml of methanol at 20° C. and at a pressure of 5 bar hydrogen in an autoclave in the pressence of Raney nickel. After the hydrogen uptake had ceased, the catalyst was removed by suction filtration, the filtrate was evaporated in vacuo, and the residue was dissolved in ethanol. The salt was precipitated with ethereal HCl and re-precipitated from ethanol/ether.

0.4 gm (10% of theory) of the desired compound was obtained; melting point 162° C.

EXAMPLE 26

Methyl 2-(2-diethylamino-ethyl)-5-(4-methoxycarbonyl-phenylamino)-2H-1,2,3-triazole-4-carboxylate hydrochloride 11.0 gm (0.04 mol) 1-(4-methoxycarbonylphenyl)-5-amino-1H-1,2,3-triazole-4-carboxylate were introduced into 150 ml of absolute dimethylformamide and reacted with 4.5 gm (0.04 mol) of potassium tert. butoxide and 5.4 gm (0.04 mol) of 1-chloro-2-diethylamino-ethane, and worked up as in Example 27.

2.4 gm (14.6% of theory of the desired compound were obtained; melting point 194° C.

Using the procedures described in Examples 1 to 26, the following end products of the formula

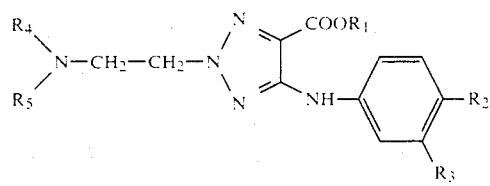

were also prepared:

| Example No. | R4\\N—/R5 | R1 | R2 | R3 | M.p °C. (hydrochloride) |
|---|---|---|---|---|---|
| 27 | (C$_2$H$_5$)$_2$N— | —CH(CH$_3$)$_2$ | Cl | H | 152 |
| 28 | (C$_2$H$_5$)$_2$N— | —CH(CH$_3$)$_2$ | Cl | Cl | 207 |
| 29 | —N(morpholino)—O | —CH(CH$_3$)$_2$ | Cl | Cl | 237 |
| 30 | (C$_2$H$_5$)$_2$N— | —CH(CH$_3$)—CH$_2$—CH$_3$ | H | Cl | 168 |
| 31 | (C$_2$H$_5$)$_2$N— | —CH(CH$_3$)—CH$_2$—CH$_3$ | Cl | Cl | 210 |
| 32 | —N(morpholino)—O | —CH(CH$_3$)—CH$_2$—CH$_3$ | Cl | Cl | 182 |
| 33 | (C$_2$H$_5$)$_2$N— | —CH(CH$_3$)$_2$ | H | Br | 191 |
| 34 | —N(morpholino)—O | —CH(CH$_3$)$_2$ | H | Br | 253 |
| 35 | (C$_2$H$_5$)$_2$N— | —CH(CH$_3$)—CH$_2$—CH$_3$ | H | Br | |
| 36 | —N(morpholino)—O | —CH(CH$_3$)—CH$_2$—CH$_3$ | H | Br | |
| 37 | (C$_2$H$_5$)$_2$N— | —CH$_2$—CH(CH$_3$)$_2$ | H | Br | |
| 38 | (C$_2$H$_5$)$_2$N— | —CH$_2$—CH(CH$_3$)$_2$ | Cl | Cl | |

-continued

| Example No. | R4\N—/R5 | R1 | R2 | R3 | M.p °C (hydro-chloride) |
|---|---|---|---|---|---|
| 39 | —N(morpholino) | —CH2—CH(CH3)2 | H | Br | |
| 40 | —N(morpholino) | —CH2—CH(CH3)2 | Cl | Cl | |

The compounds of the present invention, that is, those embraced by formula I above and their non-toxic, pharmacologically acceptable acid addition salts, have useful pharmacodynamic properties. More particularly, they exhibit sleep-potentiating activity without affecting the natural sleep rhythm and enhance the blood circulation in warm-blooded animals. Their toxicities are generally low, as has been demonstrated by toxicity tests in the mouse after intravenous and oral administration.

By virtue of those properties, the compounds of the present invention are useful as active ingredients in pharmaceutical compositions for the treatment of blood flow disorders and sleep disorders.

For pharmaceutical purposes the compounds of the present invention are administered to warm-blooded animals perorally or parenterally as active ingredients in customary pharmaceutical compositions, that is, compositions consisting essentially of an inert pharmaceutically carrier and an effective amount of the active ingredient, such as tablets, coated pills, capsules, wafers, powders, solutions, suspensions, emulsions, syrups and the like. An effective amount of the compounds according to the present invention for oral administration is from 0.05 to 50 mgm/kg body weight and for intravenous administration it is from 0.01 to 10 mgm/kg body weight, preferably 1 to 5 mgm/kg.

The following examples illustrate a few pharmaceutical compositions comprising a compound of the present invention as an active ingredient and represent the best modes contemplated of using the invention. The parts are parts by weight unless otherwise specified.

EXAMPLE 41

Coated tablets

The tablet core is compounded from the following ingredients:

| | |
|---|---|
| Methyl-2-(2-dimethylamino-ethyl)-5-(4-chlorophenyl-amino)-2H—1,2,3-triazole-4-carboxylate hydrochloride | 5 parts |
| Lactose | 65 parts |
| Corn starch | 130 parts |
| Sec. calcium phosphate | 40 parts |
| Soluble starch | 3 parts |
| Magnesium stearate | 3 parts |
| Collodial silicic acid | 4 parts |
| Total | 250 parts |

Preparation:

The active ingredient is mixed with some of the excipients, thoroughly kneaded with an aqueous solution of the soluble starch and granulated in the usual way by means of a screen. The granules are mixed with the remaining excipients and compressed into tablet cores, each weighing 250 mg, which are then coated in the usual way with a mixture of sugar, talcum and gum arabic.

EXAMPLE 42

Injection solution

The solution is compounded from the following ingredients:

| | |
|---|---|
| Methyl-2(2-diethyl amino-propyl)-5-(4-bromophenyl-amino)-2H—1,2,3-triazole-4-carboxylate hydrochloride | 1.0 parts |
| Sodium chloride | 18.0 parts |
| Distilled water | q.s.ad 2000.0 parts by vol. |

Preparation:

The active ingredient and the sodium chloride are dissolved in the distilled water, and the solution is filtered into glass ampules in an atmosphere of nitrogen.

EXAMPLE 43

Drop solution

The solution is compounded from the following ingredients:

| | |
|---|---|
| n-Butyl-2(2-dimethylamino-ethyl)-5-(4-chlorophenyl-amino)-2H—1,2,3-triazole-4-carboxylate hydrochloride | 0.02 parts |
| Methyl-p-hydroxybenzoate | 0.07 parts |
| Propyl-p-hydroxybenzoate | 0.03 parts |
| Demineralized water | q.s.ad 100.0 parts by vol. |

Preparation:

The active ingredient and the p-hydroxybenzoates are dissolved in the demineralized water, and the solution is filtered and filled into 100 cc-bottles equipped with a dropping spout.

Any one of the other compounds embraced by formula I or a non-toxic, pharmacologically acceptable acid addition salt thereof may be substituted for the particular active ingredient in Examples 41 through 43. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

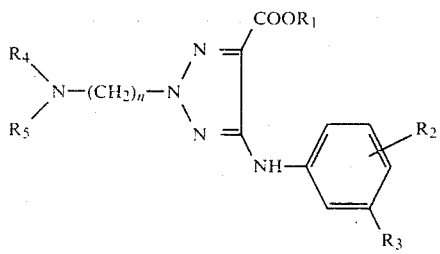

wherein
- $R_1$ is straight or branched alkyl of 1 to 4 carbon atoms;
- $R_2$ is hydrogen, halogen, amino, nitro, alkoxy of 1 to 3 carbon atoms, $-COOR_6$, 3-methyl or 4-methyl
- $R_3$ is hydrogen or halogen;
- $R_4$ and $R_5$ are each alkyl of 1 of 4 carbon atoms or, together with each other and the nitrogen atom to which they are attached, piperidino, pyrrolidino or morpholino;
- $R_6$ is alkyl of 1 to 3 carbon atoms; and
- n is 2 or 3;

or a non-toxic, pharmacologically acceptable acid addition salt thereof.

2. A compound of claim 1, which is of the formula

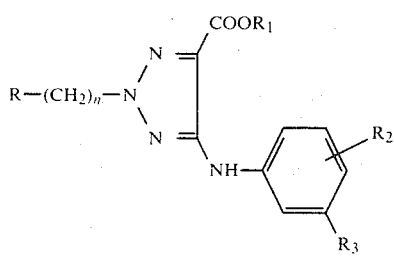

wherein
- R is dimethylamino, diethylamino, piperidino or morpholino;
- $R_1$ is straight or branched alkyl of 1 to 4 carbon atoms;
- $R_2$ is hydrogen, chlorine, 3-methyl, 4-methyl, methoxy, nitro, amino, methoxycarbonyl, 4-fluoro or 4-bromo
- $R_3$ is hydrogen or chlorine; and
- n is 2 or 3;

or a non-toxic, pharmacologically acceptable acid addition salt thereof.

3. A compound of claim 2, where
- $R$, $R_2$, $R_3$ and n have the same meanings as in claim 2, and
- $R_1$ is methyl, ethyl or n-butyl, or a non-toxic, pharmacologically acceptable acid addition salt thereof.

4. A compound of claim 2, wherein
- R is dimethylamino or diethylamino;
- $R_1$ is methyl or n-butyl;
- $R_2$ is methyl, 4-chloro or 4-bromo;
- $R_3$ is hydrogen; and
- n is 2 or 3;

or a non-toxic, pharmacologically acceptable acid addition salt thereof.

5. A pharmaceutical composition consisting essentially of an inert pharmaceutical carrier and an effective sleep-potentiating or circulation-enhancing amount of a compound of claim 1.

6. The method of potentiating the sleep or enhancing blood circulation of a warm-blooded animal in need thereof, which comprises perorally or parenterally administrating to said animal an effective sleep-potentiating or circulation-enhancing amount of a compound of claim 1.

* * * * *